US00PP16443P3

(12) United States Plant Patent
Redman

(10) Patent No.: US PP16,443 P3
(45) Date of Patent: Apr. 11, 2006

(54) ***CHRYSANTHEMUM* PLANT NAMED 'VAMP TIME IMPROVED'**

(50) Latin Name: *Chrysanthemum morifolium*
Varietal Denomination: Vamp Time Improved

(75) Inventor: Ruth Redman, Bognor Regis (GB)

(73) Assignee: Cleangro, Ltd., Chichester (GB)

( * ) Notice: Subject to any disclaimer, the term of this patent is extended or adjusted under 35 U.S.C. 154(b) by 66 days.

(21) Appl. No.: 10/993,259

(22) Filed: Nov. 18, 2004

(65) Prior Publication Data

US 2005/0114966 P1 May 26, 2005

Related U.S. Application Data

(60) Provisional application No. 60/524,337, filed on Nov. 20, 2003.

(51) Int. Cl.
*A01H 5/00* (2006.01)

(52) U.S. Cl. ..... Plt./291

(58) Field of Classification Search ..... Plt./291
See application file for complete search history.

(56) References Cited

U.S. PATENT DOCUMENTS

PP13,602 P2 2/2003 Boeder ..... Plt./291

OTHER PUBLICATIONS

2001 Ficor catalog, listing the variety 'Vamp Time'. See, e.g., pp. 4 and 7.
2002 Ficor catalog, listing the variety 'Vamp Time'. See, e.g., pp. 4 and 7.
2003 Ficor catalog, listing the variety 'Vamp Time'. See, e.g., pp. 2, 3 and 5.
2002 Van Zanten North America catalog, listing the variety 'Vamp Time'. See, e.g., pp. 7 and 8 (photograph). Also listing the variety 'Festival Time Improved'. See, e.g., pp. 5 (photograph) and 7.

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'Vamp Time Improved,' having a good uniform canopy of light pink decorative flowers. The new variety has a medium vigor, free branching, with a uniform spreading habit and good foliage presentation.

1 Drawing Sheet

Latin name of the genus and species: Botanical classification: *Chrysanthemum morifolium.*

Variety denomination: The new *Chrysanthemum* variety denomination is 'Vamp Time Improved.'

BACKGROUND OF THE INVENTION

The present invention comprises a new and distinct cultivar of *Chrysanthemum* botanically known as *Chrysanthemum morifolium,* and referred to by the cultivar name 'Vamp Time Improved.'

'Vamp Time Improved,' identified as 20544-0A, was discovered as a whole plant natural mutation in a controlled cultivated planting of the variety 'Vamp Time,' an unpatented seedling identified as 20544-0. The new variety 'Vamp Time Improved' has been asexually reproduced by vegetative cuttings in Chichester, West Sussex, United Kingdom and the distinguishing characteristics are retained through successive generations of asexual reproduction.

BRIEF SUMMARY OF THE INVENTION

'Vamp Time Improved' is a pot type of *Chrysanthemum* plant variety having light pink decorative flowers.

Comparison with Parent

Plants of the new *Chrysanthemum* variety 'Vamp Time Improved' are similar to the parent variety 'Vamp Time' in plant habitat and growth rate. In side-by-side comparisons in Chichester, West Sussex, United Kingdom, under commercial practice, plants of the new *Chrysanthemum* variety 'Vamp Time Improved' compared to plants of the parent 'Vamp Time' in the following characteristics.

1. The new variety 'Vamp Time Improved' produces light pink decorative flowers whereas the parent 'Vamp Time' also produces light pink decorative flowers.
2. Plants of the new variety 'Vamp Time Improved' have larger and taller inflorescence than plants of the parent variety 'Vamp Time.'
3. Plants of the new variety 'Vamp Time Improved' have a slower response time than the parent 'Vamp Time.'

Comparison with Other Varieties

Plants of the new *Chrysanthemum* variety 'Vamp Time Improved' are similar to the variety 'Festival Time Improved' (U.S. Plant Pat. No. 13,602) in plant habitat and growth rate. However, in side-by-side comparisons in Chichester, West Sussex, United Kingdom, under commercial practice, plants of the new *Chrysanthemum* variety 'Vamp Time Improved' differed from plants of 'Festival Time Improved' in the following characteristics.

1. The new variety 'Vamp Time Improved' produces pink decorative flowers whereas the variety 'Festival Time Improved' produces light pink decorative flowers with a dark pink center.
2. Plants of the new variety 'Vamp Time Improved' have larger and taller inflorescence than plants of 'Festival Time Improved.'

BRIEF DESCRIPTION OF ILLUSTRATION

Typical specimens of the plant and flowers for the new *Chrysanthemum* variety 'Vamp Time Improved' are shown in the accompanying digital photograph. The colors shown are as true as possible within the usual limits of this kind of illustration.

FIG. 1 is a whole plant view of the new variety 'Vamp Time Improved' grown in a pot. The plant shown in the illustration is 58 days from the commencement of Short Days.

DETAILED BOTANICAL DESCRIPTION

The following description of the new *Chrysanthemum* variety 'Vamp Time Improved' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 gm per liter. To produce a commercial product the plants may be pinched once with the center bud removed. The typical container size for commercial growth is 1 liter. It has been observed that the shelf life of the new variety is about 25 days with a response time of about 8.5 weeks. The new variety is suitable for growth in a temperature range of 15° C. to 25° C.

The new variety may be produced as a spray. The following description is with respect to a plant produced as pot. In the description of this new *Chrysanthemum* variety, color values have been taken from The Royal Horticultural Society Colour Chart (R.H.S.C.C.).

Plant

Plant type: Pot.
Habit: Upright and free branching.
Height: 23 cm.
Width: 32 cm.
Stem:
- *Length* (*cm*).—5.5.
- *Diameter* (*cm*).—0.8.
- *Texture.*—Slightly pubescent.
- *Color.*—138B.

Branching characteristics: Upright and free branching.
Length of lateral branches:
- *Length* (*cm*).—12.
- *Diameter* (*cm*).—0.5.
- *Texture.*—Slightly pubescent.

Number of breaks from pinch: 4.
Response time: 58 days.
Vigor: Medium.
Shelf life: 25 days.
Disease/pest (susceptibility/resistance observed): None observed to date.
Drought and temperature (susceptibility/resistance observed): None observed to date.
Growth retardant type and treatment: 3 applications of 2.5 gm/liter B9 @ 2, 21 and 28 days after sticking of unrooted cuttings.
The plants were grown for 2 weeks in Long Day conditions (20 hours of light) and then transferred to Short Day conditions (13 hours of dark).
Propagation:
- *Type.*—Vegetative Propagation via Stem Cuttings.
- *Time to rooting.*—14 days with soil temperatures of 18° C.
- *Rooting habit.*—After 7 days the first roots emerge and form root primordia. In 14 Long Days a complete root system is developed.

Foliage

Number of leaves per lateral branch: 9.
Compound or single: Single.
Arrangement of leaves: Alternate.
- *Shape of leaf.*—Typically 5 lobed.
- *Size of leaf.*—Width (cm): 4.5 Length (cm): 7.
- *Leaf apex.*—Acute.
- *Base.*—Cordate.
- *Attachment.*—Petioled.
- *Aspect.*—Slightly undulating.
- *Margin.*—Lobed.
- *Surface characteristics.*—Top: slightly pubescent. Bottom: pubescent.

Petiole:
- *Color.*—138A.
- *Length.*—1.3 cm.
- *Diameter.*—0.2 cm.

Venation:
- *Color.*—Upper side: 147C. under side: 147C.

Color:
- *Mature leaf, upper side.*—Near 137A; under side: near 137C.
- *Young leaf, upper side.*—Near 147A; under side: near 137C.

Flower

Flower appearance: Matte.
Flower type: Decorative.
Flower form: Domed.
Flower shape: Round.
Flowering habit: Domed capitulum.
Number of blossoms per branch: 4.
Typical and observed flowering season: January to December.
Inflorescence form: Cyme.
- *Depth of fully expanded blossoms.*—1.5 cm.
- *Diameter of fully expanded blossoms.*—9 cm.

Phyllaries:
- *Number.*—13.
- *Color.*—Near 138A.
- *Length.*—0.7 cm.
- *Width.*—0.4 cm.
- *Texture/appearance.*—Pubescent.

Peduncle:
- *Length.*—8.5 cm.
- *Diameter.*—0.6 cm.
- *Angle from stem* (*degrees*).—15.
- *Color.*—Near 138B.
- *Surface.*—Slightly pubescent.
- *Habit.*—Slightly undulating.
- *Strength.*—Medium.

Pedicel:
*Length.*—Terminal: 3 cm; lateral: 3.5 cm.
*Diameter (cm).*—0.3 cm.
*Color.*—Near 138B.
*Surface.*—Slightly pubescent.
*Habit.*—Slightly undulating.
*Strength.*—Medium.
Ray florets:
*Form/shape.*—Straight.
*Texture/appearance.*—Matte.
*Number per flower.*—95.
*Length.*—4 cm Width: 1.3 cm.
*Apex.*—Dentate.
*Base.*—Tapered.
*Margin.*—Entire.
Disc florets:
*Form/shape.*—Cylindric.
*Texture/appearance.*—Shiny.
*Number per flower.*—14.
*Length.*—0.5 cm; Width: 0.1 cm.
*Diameter of disc.*—0.3 cm.
Fragrance: None observed.
Flower bud (at onset of color):
*Length.*—1.8 cm.
*Diameter.*—1.5 cm.
*Form/shape.*—Spherical.
General flower color:
1. *Ray florets, upper side.*—Immature: near 65B. Mature: near 65C. Older/Fading: near 65D.
2. *Ray florets, under side.*—Immature: near 65C. Mature: near 65C. Older/Fading: near 65D.
3. *Disc florets.*—Immature: near 145B. Mature: near 145B. Older/Fading: near 145C.
4. *Bud.*—65A.

Flower progression with age: There is no change with the flower form, but there is a slight color fading with age.

Reproductive Organs

Gynoecium present on Ray and Disc florets.
Ray florets per individual flower:
*Pistil number.*—95.
*Stigma color.*—Near 3A.
*Stigma shape.*—Forked.
*Style color.*—Near 154B.
*Style length.*—0.4 cm.
Disc florets per individual flower:
*Pistil number.*—14.
*Stigma color.*—Near 3A.
*Stigma shape.*—Forked.
*Style color.*—Near 154B.
*Style length.*—0.4 cm.
Androecium: None observed.
Fruit and seeds: None observed.

What is claimed is:

1. A new and distinct variety of *Chrysanthemum* plant, substantially as described and illustrated herein.

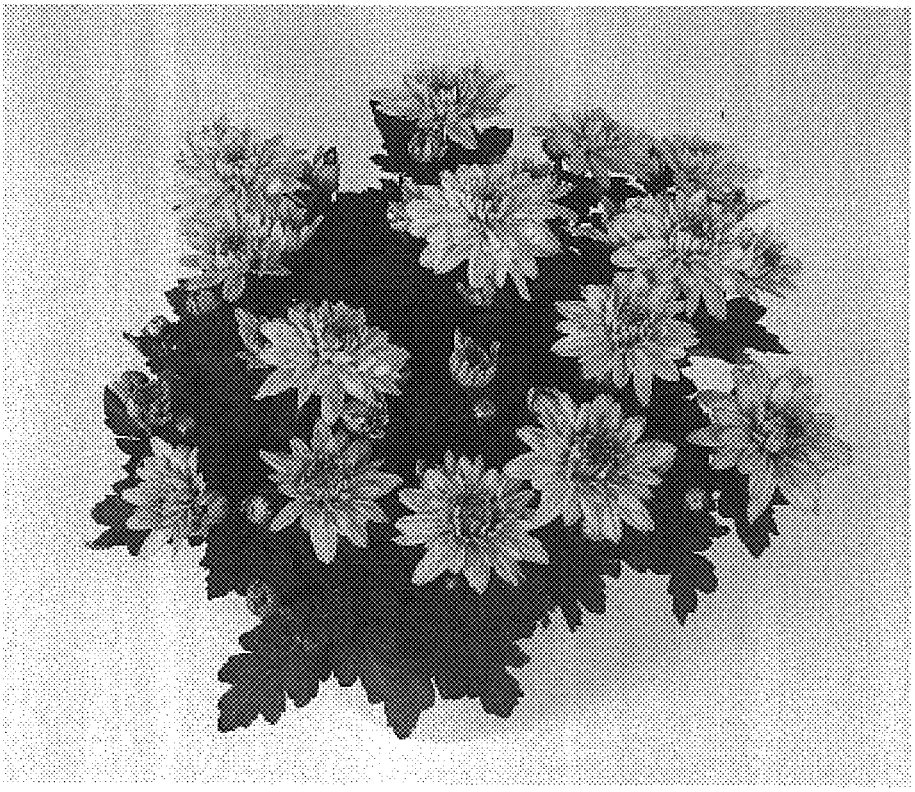

* * * * *